United States Patent [19]

Martin et al.

[11] Patent Number: 4,802,487
[45] Date of Patent: Feb. 7, 1989

[54] ENDOSCOPICALLY DELIVERABLE ULTRASOUND IMAGING SYSTEM

[75] Inventors: Roy W. Martin, Redmond; Fred E. Silverstein, Seattle, both of Wash.

[73] Assignee: Washington Research Foundation, Seattle, Wash.

[21] Appl. No.: 30,898

[22] Filed: Mar. 26, 1987

[51] Int. Cl.$^4$ .............................................. A61B 10/00
[52] U.S. Cl. ................................... 128/662.06; 128/4
[58] Field of Search ............... 128/660, 661, 663, 4–6

[56] References Cited

U.S. PATENT DOCUMENTS

| | | | |
|---|---|---|---|
| 3,777,740 | 12/1973 | Hohanson | 128/663 |
| 4,184,094 | 1/1980 | Kopel | 128/660 X |
| 4,205,686 | 6/1980 | Harris et al. | 128/660 |
| 4,321,915 | 3/1982 | Leighton et al. | 128/4 |
| 4,417,583 | 11/1983 | Bechai et al. | 128/4 X |
| 4,532,933 | 8/1985 | Hohanson | 128/660 |
| 4,607,619 | 8/1986 | Scibe et al. | 128/4 |

FOREIGN PATENT DOCUMENTS 2315056  10/1974  Fed. Rep. of Germany .......... 128/4

OTHER PUBLICATIONS

Hisanaga, K. et al, "A Transesophageal Real-Time Sector Scanner with an Oil-Filled Ell", Proceedings of the 23rd Ann. Meeting of the AIUM, p. 47.

Hisanaga, K. et al, "A New Transesophageal Real-Time Linear Scanner & Initial Clin. Results", Proc. of the 23rd Ann. Meeting of the AIUM, p. 112.

Hisanaga, K. et al, "A New Trans-Digestive Tract Scanner with a Gastro-Fiber-Scope", Proc. of the 23rd Ann. Meeting of the AIUM, p. 103.

McCormache, T. et al, "Doppler UTS Probe for Assessment of Bloodflow in Oesophageal Varices", Lancet 3/26/83.

*Primary Examiner*—Francis J. Jaworski
*Attorney, Agent, or Firm*—Seed and Berry

[57] ABSTRACT

An endoscopically deliverable ultrasound imaging system having an ultrasound probe mounted at the end of an endoscopically deliverable catheter. The catheter connects the probe to an ultrasound imaging system. The axial or radial position of the ultrasound probe is measured by a position transducer mounted on the endocscope adjacent the biopsy port from which the catheter extends. The output of the position measuring transducer is applied to the ultrasound imaging system so that the imaging system provides an image of the tissue depth as a function of the position of the ultrasound probe.

44 Claims, 9 Drawing Sheets

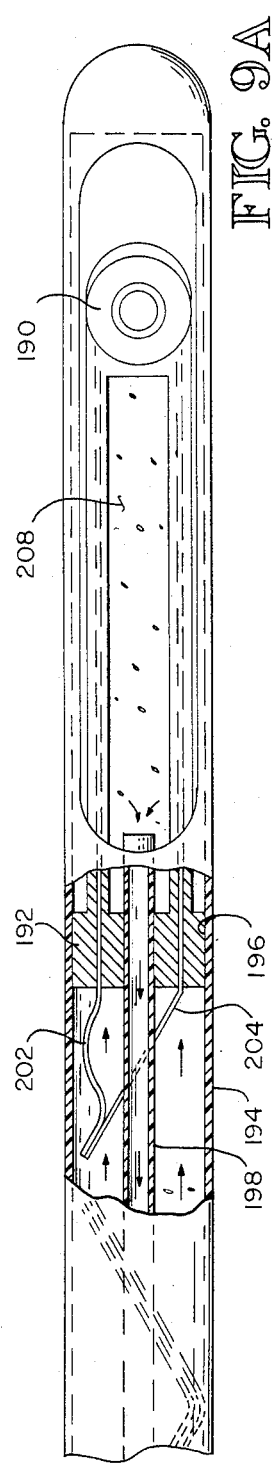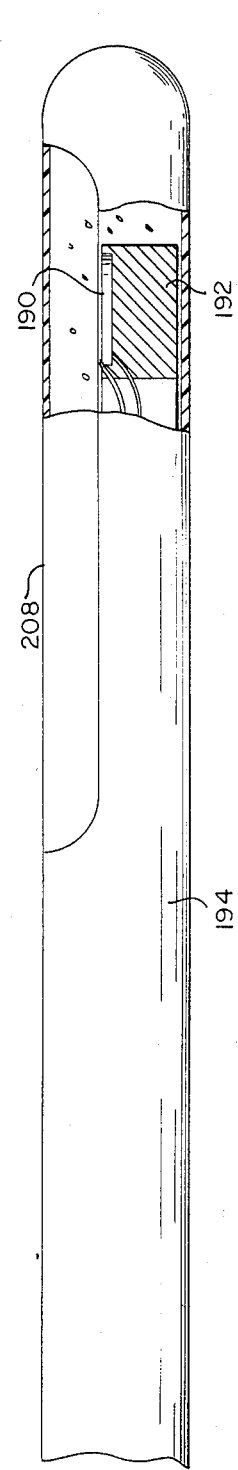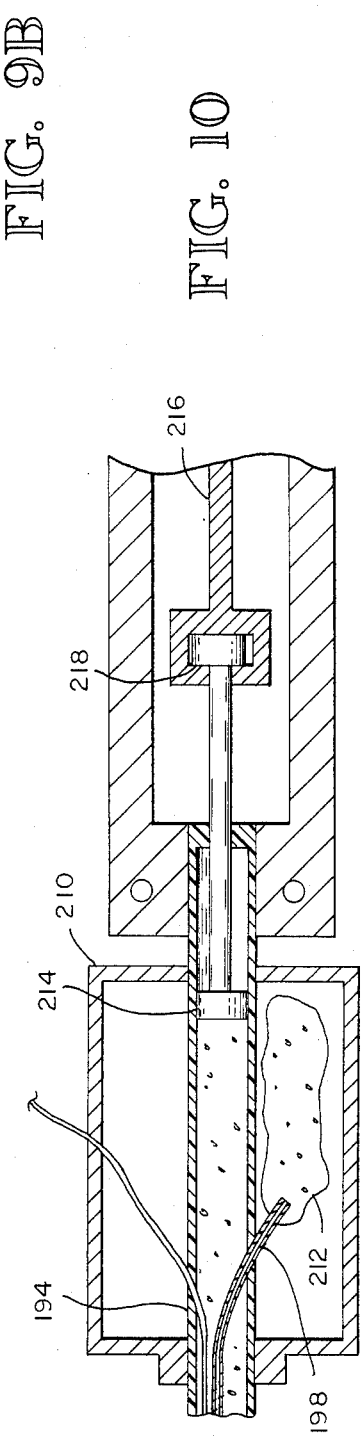

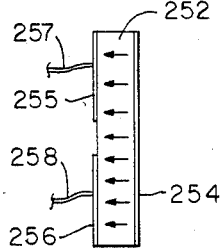
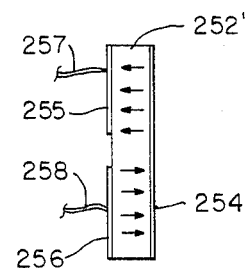
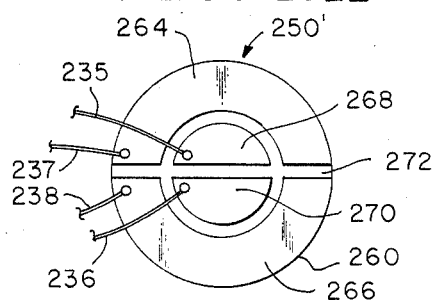
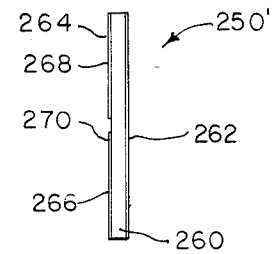
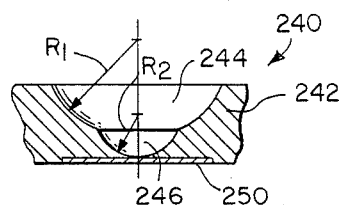
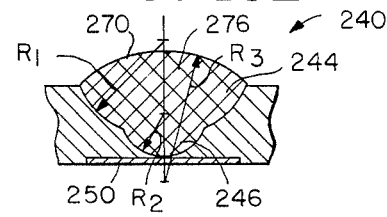
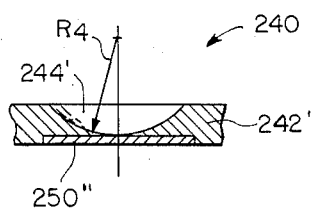
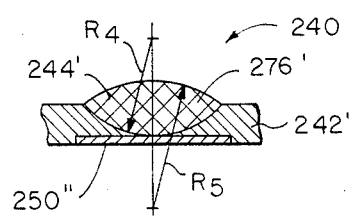

ENDOSCOPICALLY DELIVERABLE ULTRASOUND IMAGING SYSTEM

This invention was supported with U.S. Government Grant No. AM 34814, initiated under the National Institutes of Health.

TECHNICAL FIELD

This invention relates to ultrasound imaging, and more particularly, to a system for ultrasonically imaging internal body tissues using an endoscopically deliverable imaging probe.

BACKGROUND ART

A wide variety of ultrasound systems have long been used for medical diagnostic purposes. One of these ultrasound devices is the Doppler probe, in which ultrasound energy is transmitted into the body and the change in frequency of the return signal is detected to provide an indication of blood flowing in veins and arteries. The characteristics of the frequency-shifted Doppler signal indicate the presence of an adjacent blood vessel and identify whether the vessel is a vein or an artery. Recently, an endoscopically deliverable ultrasound Doppler probe has been proposed and is described in U.S. Pat. No. 4,582,067, to Silverstein et al. The endoscopically deliverable Doppler probe can be passed through the biopsy channel of standard endoscopes and placed, under direct vision, against the tissue to be examined. The system has been found to be useful for evaluating the papilla of Vater to determine whether an abnormal blood vessel is present which might cause life-threatening hemorrhage. The system has also been used for locating arteries in ulcers that are responsible for massive upper gastrointestinal hemorrhage before and after the application of endoscopically delivered hemostatic therapy.

Another conventional, commonly used ultrasound system allows subcutaneous tissues to be visualized. In ultrasound imaging, an ultrasound transducer is generally placed in contact with the skin of the patient and pulses of ultrasound energy are transmitted from the transducer into the tissues of interest. Return echoes from the tissues are localized to a specific depth by conventional range gating and used to modulate the intensity of a cathode-ray tube display as the probe is either electrically or mechanically scanned across the tissues. The scan of the probe modulates one axis of the CRT, while the other axis of the CRT is modulated by the range gate. The CRT thus displays a cross section of tissue. The internal organs are visible primarily as a result of the changes in the acoustic impedance of such organs in comparison to the surrounding tissues.

Ultrasound imaging has also been combined with the Doppler principle to image blood flowing veins and arteries. In ultrasound Doppler imaging, returns from non-moving tissues and organs are either ignored or processed separately to display return echoes from moving blood.

Although tissues and internal organs, particularly those close to the surface, can be imaged externally, the walls of the gastrointestinal track cannot be externally imaged with any degree of accuracy for several reasons. First, the wall of the gastrointestinal tract moves toward and away from the transducer, thus making it extremely difficult to isolate the relatively small thickness of the GI track as the depth of interest. Furthermore, deep ultrasound imaging can be effectively accomplished only by utilizing relatively low frequencies. However, the high resolution required to usefully image the walls of the GI track require a substantially higher ultrasound frequency. Yet this higher ultrasound frequency is quickly attenuated in the body and never reaches the walls of the GI track of interest.

In order to allow the walls of the gastrointestinal track to be ultrasonically imaged without the many problems of external imaging, attempts have been made to endoscopically image such tissues. Internal ultrasound imaging offers several advantages over percutaneous ultrasound and other imaging techniques. With internal ultrasound imaging, penetration is less of a problem when the transducer is placed immediately adjacent to the tissue target. The anterior abdominal wall and other intervening structures do not have to be penetrated. Intervening structures, especially air, can severely limit the percutaneous ultrasound in certain clinical situations. The reduced penetration requirement allows for the use of highfrequency ultrasound, which is capable of producing images of high resolution. High-resolution ultrasound may reduce exposure to ionizing radiation from other diagnostic procedures by eliminating other less specific tests. Although ultrasound does have biological effects, for use at diagnostic levels no significant effects have been reported.

There is a critical need to be able to obtain during routine endoscopy information about wall structure. This data may be useful to guide the next diagnostic or therapeutic steps while the endoscope is still in place. The earlier diagnosis which internal ultrasound imaging would allow could have highly desirable effects upon the treatment of the patient in terms of directing appropriate effective therapy and avoiding inappropriate therapy. The advantages of an early, specific, inexpensive, and noninvasive diagnosis are well recognized. For example, if the exact extent of wall involvement by a sessile tumor could be determined, tumors that could be ablated endoscopically without causing perforation could be easily identified. Given the decision that the disease is localized to the mucosa without deep invasion, laser or electrocautery could be applied. If, however, the ultrasound image indicated that the tumor had spread to adjacent structures, then palliative therapy would be appropriate.

Internal ultrasound imaging is particularly appropriate for diseases which have certain common characteristics. Diseases which involve the gastrointestinal wall, diseases which can be reached endoscopically, diseases that are frequent, disabling, and currently not readily diagnosed, and diseases that are now poorly treated because they are diagnosed too late are all prime candidates.

One disease that could be advantageously diagnosed by internal ultrasound imaging is Crohn's inflammatory bowel disease. Crohn's disease is a disabling inflammatory disease of the gastrointestinal track which affects the small and large bowel. The cause is unknown. It is one of the most frequently encountered types of inflammatory bowel disease, the other being mucosal ulcerative colitis. However, Crohn's disease involves the entire thickness of the bowel wall (transmural disease), whereas ulcerative colitis is limited to the mucosa of the colon. It has been estimated that between one million and two million Americans have inflammatory bowel diseases, and the frequency of these diseases is increasing. Most of the new cases are diagnosed before the age of thirty. Crohn's disease is difficult to diagnose and treat. When the patient first presents, the work-up may include history, physical exam, sigmoidoscopy, barium enema and small intestine X-rays, colonoscopy, and rectal biopsy. Even with this evaluation, diagnosis may be uncertain. Symptoms and complications are variable. By rapidly examining the wall of the rectum and colon with internal ultrasound imaging, an early specific diagnosis may be made. When following such patients, internal ultrasound imaging may also provide an essential parameter to evaluate whether the disease to adjacent structures or formed an abscess.

Gastric malignancies, including adenocarcinoma and lymphoma, may also be diagnosed using internal ultrasound imaging. Tumors of the upper gastrointestinal tract are frequent. Currently, gastroenterologists use endoscopy to evaluate the patient with epigastric symptoms suggesting an ulcer or tumor. After visually inspecting an abnormal area, biopsies and brush cytologies are taken. However, it is impossible for an endoscopist to evaluate the area of the submucosa. There may be a lump, but the biopsies will often contain only normal surface mucosa from over the mass. If a cancer is suspected, the endoscopist cannot assess the degree of extension of the tumor. Internal ultrasound imaging could be used routinely during diagnostic endoscopy. Once an abnormal area was visualized, an ultrasound probe could determine the nature of the underlying wall. It could also answer such questions as whether there is a mass present, whether the mass is abnormally thick, whether there are abnormal lymph nodes adjacent to the stomach, or whether there are other diagnostic features. This information might allow an earlier diagnosis, expedite correct therapy, and avoid unnecessary intervention.

Internal ultrasound imaging may also be applicable to esophageal carcinoma. Tumors of the esophagus have posed a significant problem for the clinician for years. When a patient presents with symptoms caused by cancer, the tumor is usually too expensive to be surgically resectable. The result is that only 39% of esophageal cancers are considered resectable and the five-year survival rate is only about 5%–10%. Since internal ultrasound imaging would allow the endoscopist to evaluate an area which is equivocal, the image might reveal diagnostic thickening of the mucosa consistent with carcinoma. It can evaluate an obvious cancer to determine whether the cancer has extended into the mediastinum, which would make the patient inoperable. Internal ultrasound imaging may also be especially helpful in the patient with a premalignant condition of the esophagus, such as Barrett's epithelium, by early detection of possibly treatable adenocarcinomas.

Tumors of the colon and rectum are one of the most common visceral tumors in the Western Hemisphere. The instance of colon and rectal cancer has increased over the past several years, and these tumors are now among the three most frequent tumors in the United States. Colon and rectal cancers account for approximately 15% of all newly diagnosed cancers in both men and women in the United States. Significant progress in early detection of these lesions has been made by screening stools for blood and by using sigmoidoscopy and colonoscopy. However, it is usually difficult to stage carcinomas of the colon and rectum preoperatively, despite CT scans and other methods. But staging can be very important for patient management. The extent of the tumor may dictate whether or not it is appropriate to use preoperative radiation therapy. Internal ultrasound imaging could be used to provide staging.

Finally, there is increasing interest in the motility of the gastrointestinal tract since many diseases which trouble patients seem related to motility. Such diseases include esophageal spasm, achalasia, abnormal gastric emptying, functional bowel disease, and other motility disfunctions.

Attempts have been made to provide internal ultrasound imaging through endoscopes using linear arrays, phased arrays, and mechanical sector scanners. The mechanical sector scanner endoscope, as described in Hisanaga, "A New Trans-Digestive-Tract Scanner with a Gastro-Fiber-Scope," *Proc.* 23 AIUM 1978, uses a specially designed, side-viewing endoscope having a transducer mounted on the end of a wire. The transducer has a transversely directed beam pattern, and it is rotated about the longitudinal axis of the endoscope by externally rotating the wire. A potentiometer is coupled to the wire and generates an electrical output indicative of the angular position of the transducer and hence the transducer beam angle. The transducer may be connected to a conventional Doppler imaging system to produce sector images of the walls of the GI track. While this device can produce images of the GI track wall, it nevertheless exhibits a number of inherent disadvantages. Many of these disadvantages stem from the integral nature of the endoscope and ultrasound probe combination. The endoscope, rather than being a relatively inexpensive, general purpose design, is specially designed to accommodate the ultrasound probe. As a result, the instrument is substantially more expensive than conventional endoscopes. Further, the ultrasound endoscope is delicate, and if damage occurs to either the optical endoscopic system or the ultrasound system, the device must undergo expensive repair. The relatively high expense inherent in a dedicated endoscope precludes the possibility of several combinations of endoscope and ultrasound systems. Another problem with dedicated endoscopes is the need to withdraw a conventional endoscope when potentially abnormal tissue is visualized in order to reinsert the dedicated endoscope to ultrasonically examine the tissue of interest. Still another problem with the mechanical scanner described in the Hisanaga article is the need for the endoscope to be a side-viewing endoscope. It is not possible to fit an end-viewing endoscope with a rotating transducer because the endoscope diameter would not be sufficient to allow the optical light and visual bundles to pass alongside a mechanical transducer. For this reason, the transducer must be at the end of the endoscope and the endoscope must be of the side-viewing variety. This disadvantage is serious because an end-viewing endoscope is more familiar to endoscopists and it is easier to use. The use of a side-viewing endoscope causes images near the tip of the endoscope to be lost. Near-field imaging can be improved only by inflating a water balloon standoff to space the tissue of interest away from the tip of the endoscope. Finally, the rotation of the wire and transducer creates a gyroscopic effect, which makes control of the endoscope difficult.

Another endoscopically deliverable ultrasound imaging system utilizes an endoscopically deliverable ultrasound probe having a linear array of transducer elements. In this system, the transducer elements are arranged in a longitudinally extending strip positioned along one wall of the endoscope, either at the tip of the endoscope or some distance from the end of the endoscope, thereby allowing the endoscope to double back and view the tissue adjacent the array. The elements of the array are then used to image the tissue in contact with the transducer elements, either sequentially or in combination using phased array techniques. Although the use of an array of transducer elements avoids the gyroscopic problem caused by rotating the transducer, it nevertheless has its own set of inherent problems. The use of an elongated array makes the transducer relatively rigid, thus making it difficult to pass into certain areas, such as into the esophagus and the duodenum. Moreover, when the linear array is positioned near the end of the endoscope, it is impossible to view the tissue of interest positioned in contact with the ultrasound array. Additionally, the use of multiple transducer elements requires a large number of conductors extending through the endoscope, thus resulting in a relatively thick endoscope, with its attendant patient discomfort. Finally, endoscopes employing a linear array are, of course, dedicated instruments, with all of the attendant problems attributed above to dedicated rotating transducer endoscopes.

Still another variety of endoscopically deliverable ultrasound scanners are phased array transducers having a series of elements parallel to each other, with the phase of the ultrasound signal transmitted to and received from the elements delayed with respect to each other. The delay makes it possible to steer the ultrasound beam and move it in an arc at a rapid rate. Phased array ultrasound imaging has been primarily used to image the heart via the esophageal wall for transesophageal echo cardiography. The wide field of the phased array probe is ideal for this application since it is essential to see as much as possible of the heart and its larger vessels. The wide field of phased array ultrasonic imaging is unsuitable for use in intestinal wall examinations.

Endoscopic ultrasound imaging requires that the ultrasound probe be very small yet still have the necessary electrical properties. Further, because of the need to image tissue positioned adjacent to the probe with high resolution, the design of the probe becomes critical. In the past, ultrasound probes consisting of a circular plate of piezoelectric material having plated front and back faces have been used. The ultrasound signal is applied to and received from contacts connected to the front and back faces of the transducer. However, because of the small diameter of such transducers, the point where the connecting wire is soldered or conductive-epoxied to the plating on the front face of the transducer may occupy a large part of the active front face of the transducer. Also, the epoxy or solder connection and wire may protrude a large fraction of a wavelength from the surface and thus alter the radiation pattern. The protrusion of the solder, epoxy, or wire also may prevent the use of single or quarter-wave matching layers since the protruding structure prevents the matching layer from fully contacting the active front face of the transducer. Another problem with connecting a wire to the front face of a transducer is that such connection prohibits the use of printed circuit boards for complete direct transducer wiring.

In order to obviate the above-described problems with connecting a wire to the active front face of a transducer, "back face only connected" transducers have been developed. In these "back face only connected" transducers, the conductive plating on the back face of a disk is separated into two semicircular areas and a wire is then connected to each of these semicircular areas. Significantly, no wire is connected to the active front face of the transducer. This prior art transducer operates by capacitively coupling the ultrasound signals to the active front face through the piezoelectric disk. For a piezoelectric disk that has been polarized in the normal manner (i.e., the entire disk polarized in one direction), one-half of the piezoelectric disk is in contraction, while the other half is in expansion. This mode of operation contrasts sharply with the usual mode of operation of piezoelectric transducers wherein the entire transducer is in either contraction or expansion. As a result, one-half of the transducer radiates waves that are 180 degrees out of phase with the waves radiated by the other half of the transducer. The transducer thus produces two main beam patterns instead of one, as would be desirable for ultrasonic imaging.

DISCLOSURE OF THE INVENTION

It is an object of the invention to provide an endoscopically deliverable ultrasound probe that can be used with virtually any general purpose endoscope.

It is another object of the invention to provide an endoscopically deliverable ultrasound imaging system that is relatively inexpensive, durable, and compact.

It is still another object of the invention to provide an endoscopically deliverable ultrasound probe that easily allows the position and orientation of the probe's transducer to be easily seen through the endoscope.

It is another object of the invention to provide an endoscopically deliverable ultrasound imaging system in which the endoscope is flexible throughout its length to make it easy to pass into organs such as the esophagus and duodenum.

It is another object of the invention to provide an endoscopically deliverable ultrasonic probe that does not adversely affect the ease of manipulating the endoscope.

It is still another object of the invention to provide an ultrasound transducer that avoids any connection to the active front face of the transducer yet generates a single ultrasound beam.

It is a further object of the invention to provide an ultrasound transducer that does not have any connection to its active front face yet generates an ultrasound beam that focuses in two discrete ranges.

These and other objects of the invention are provided by a system for ultrasonically imaging internal tissues through the biopsy channels of conventional endoscopes. The system includes a catheter having a diameter that is sufficiently small to pass through the biopsy channel of the endoscope. An ultrasound transducer is mounted at one end of the catheter. The ultrasound transducer also has a diameter that is sufficiently small to pass through the biopsy channel of the endoscope. The transducer preferably has a transversely directed beam pattern. A position sensor coupled between the endoscope and the catheter measures the longitudinal position of the catheter with respect to the endoscope. An imaging system is connected to the transducer through conductors extending through the catheter. The imaging system generates an ultrasound signal that is applied to the transducer to direct ultrasound energy into the tissue of interest. Return echoes from the tissue are received by the transducer to generate an ultrasound signal. The amplitude of the ultrasound signal preferably modulates the intensity of a cathode-ray tube. The transit time of the echo signal is indicative of the tissue's depth, which modulates one axis of the cathode-ray tube, while the other axis of the cathode-ray tube is modulated by the output of the position sensor. A cross-sectional image of the GI wall in contact with the transducer is thus generated.

BRIEF DESCRIPTION OF THE DRAWINGS

FIG. 9 is a cross-sectional view of an ultrasound probe that is automatically scanned hydraulically by fluid delivered through the catheter.

FIG. 10 is a cross-sectional view of a mechanism for generating the hydraulic signal applied to the automatically scanned ultrasound probe of FIG. 9.

FIGS. 14A and 14B are plan and elevational views of a dual-focal-length ultrasound transducer used in the ultrasound probe of the endoscopically deliverable ultrasound imaging system.

FIGS. 15A and 15B are cross-sectional views of a conventional "back face only connected" ultrasound transducer and the inventive "back face only connected" ultrasound transducer.

FIGS. 16A and 16B are cross-sectional views of a dual-element ultrasound probe showing the manner in which the ultrasound lens is formed.

FIGS. 17A and 17B are cross-sectional views of a single-element ultrasound probe showing how the ultrasound lens is formed.

BEST MODE FOR CARRYING OUT THE INVENTION

The endoscopically deliverable ultrasound imaging system consists of a number of components, all of which are described in detail below. The system includes an ultrasound probe mounted at the end of a catheter that is routed through the biopsy channel of a conventional endoscope. The system further includes an ultrasound probe position transducer that generates an output indicative of the axial or rotational position of the ultrasound probe. Finally, the system includes an ultrasound imaging device, which may be of conventional design, that is connected both to the ultrasound probe through the catheter and to the ultrasound probe position transducer.

Figure 1:
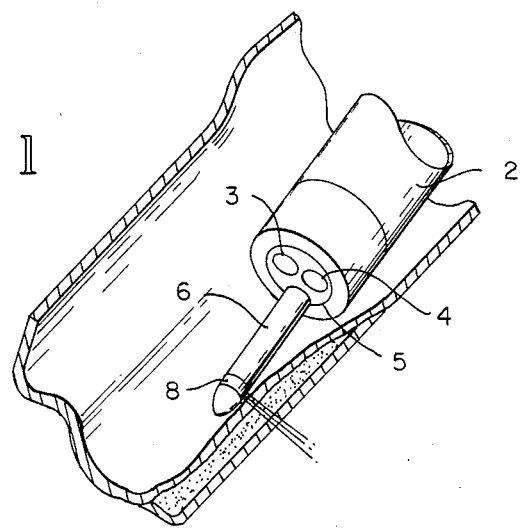
FIG. 1 is an isometric view showing the endoscopically deliverable ultrasound probe in operation, imaging varices in the esophagus.

The endoscopically deliverable ultrasound imaging system is illustrated in use in FIG. 1. Although the inventive imaging system can be used to examine a wide variety of tissues, it is shown in use examining varices on the wall of the esophagus. Also shown is a conventional endoscope 2 having an illuminating window 3, a viewing window 4, and biopsy channel 5. A specially designed catheter 6, described in greater detail below, extends through the biopsy channel 5 and terminates in a specially designed ultrasound transducer 8, also described in greater detail below. The transducer 8 is placed in contact with the esophageal varices and a high-frequency electrical signal is applied to the transducer 8 to generate an ultrasound beam. The ultrasound beam is reflected from the esophageal wall to the transducer 8, which then converts the reflected ultrasound energy to an electrical signal. The transducer 8 is scanned across the esophageal varices in one of two modes. In an axial scan mode, the transducer 8 is moved along the axis of the catheter 6 by causing the catheter 6 to move into and out of the biopsy channel 5. In the radial scan mode, the catheter 6 is rotated back and forth to cause the transducer 8 to scan in a radial pattern. The ultrasound image is generated by displaying the ultrasound returns in one axis and the axial or radial position of the transducer 8 along the other axis.

Figure 2:
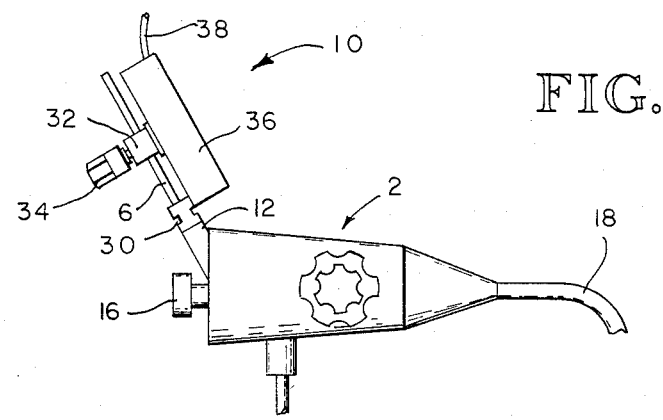
FIG. 2 is a plan view of the endoscopically deliverable ultrasound imaging system showing one embodiment of an ultrasound probe position transducer mounted on a conventional endoscope.

One embodiment of a position transducer for measuring the axial position of the ultrasound probe is illustrated in FIG. 2. The position transducer 10 is mounted on the proximal biopsy port 5 of the endoscope 2, which, as is well understood in the art, includes a conventional eyepiece 16 allowing optical communication through the endoscope body 18. The position transducer 10 is mounted on the proximal biopsy port 12 by a conventional leurlock assembly 30. The catheter 6 extends from the biopsy port through a bore in a tubular boss 32. The boss 32 threadably receives a thumbscrew 34, which may be rotated to cause the end of the thrumbscrew 34 to frictionally engage the catheter 6 within the bore in the tubular boss 32. The tubular boss 32 is mounted on the wiper arm of a conventional slide potentiometer 36, which, as is well known in the art, has a resistance between leads 38 that varies with the linear position of the wiper arm.

In operation, the catheter 6 is moved axially so that the ultrasound probe is in the proper position, as verified by looking through the eyepiece 16 of the endoscope 2. During this procedure, the thumbscrew 34 is disengaged from the catheter 6 so that the output of the potentiometer 36 remains constant. As a result, large axial movement of the catheter 6 may be accomplished without varying the output of the position transducer 36. When the ultrasound probe is in the proper position, as verified by viewing the probe through the eyepiece 16 of the endoscope 2, the thumbscrew 34 is rotated to frictionally engage the catheter 6. Thereafter, axial movement of the catheter 6 produces a corresponding movement of the wiper arm of the potentiometer 36. As a result, the resistance between the leads 38 varies as a linear or other function of the axial position of the ultrasound probe. As explained in greater detail below, the ultrasound probe is moved axially across the tissue to be examined, and ultrasound returns from the ultrasound probe illustrative of the tissue beneath the probe are plotted horizontally on a conventional cathode-ray tube display. The output of the potentiometer 36 modulates the vertical axis of the cathode-ray tube so that the cathode-ray tube displays an image of tissue depth on the horizontal axis and ultrasound probe position on the vertical axis.

Figure 3:
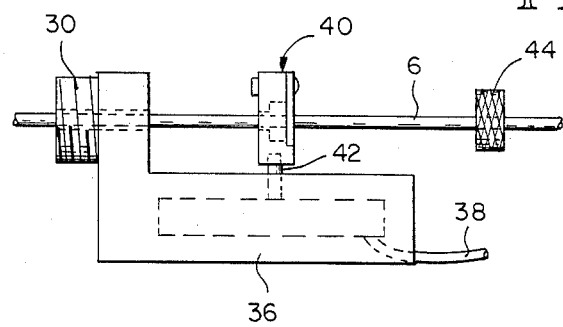
FIG. 3 is an elevational view of another embodiment of an ultrasound probe position transducer.
Figure 4A:
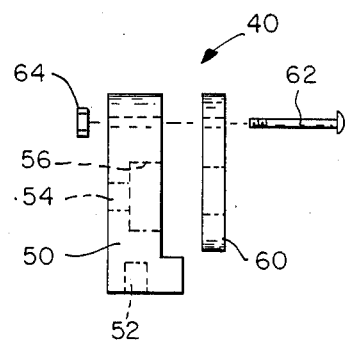
FIGS. 4A-4D are elevational and plan views of the various components of the position transducer of FIG. 2.
Figure 4B:
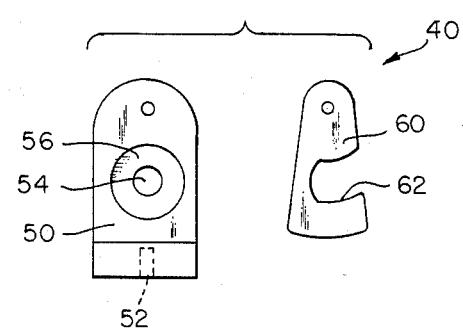
Figure 4C:
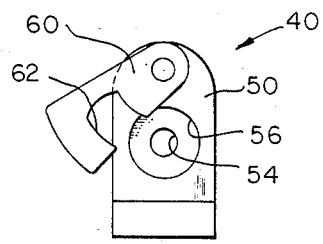
Figure 4D:
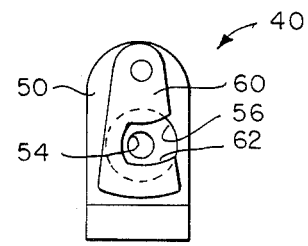
Figure 5A:
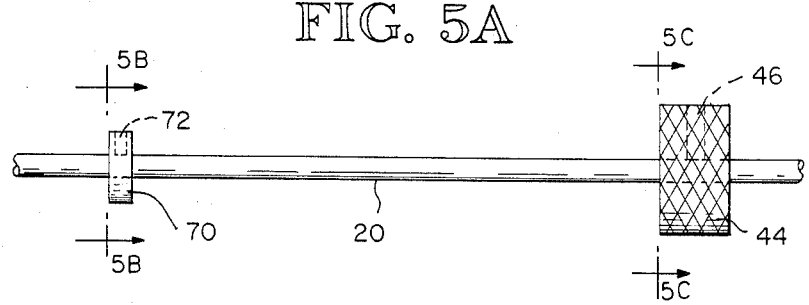
FIGS. 5A-5C are elevational and plan views of mechanisms mounted on the ultrasound probe catheter for rotating the catheter and restricting its axial movement.
Figure 5B:
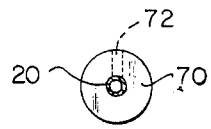
Figure 5C:
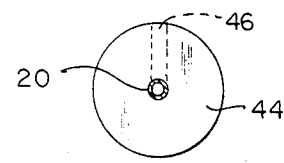

Another embodiment of an ultrasound probe position transducer is illustrated in FIGS. 3-5. The embodiment of FIGS. 3-5 differs from the embodiment of FIG. 2 primarily in the manner in which the catheter 6 is releasibly secured to the position-measuring transducer. Thus, as with the embodiment of FIG. 2, the embodiment of FIGS. 3-5 utilizes a linear potentiometer 36 mounted on the biopsy port 12 of a conventional endoscope 2 through a conventional leurlock connector 30. A connector assembly 40, described in greater detail below, is mounted on a wiper arm 42 of the potentiometer 36. A knurled knob 44 is fixedly mounted on the catheter 6 by conventional means, such as a setscrew 46 (FIGS. 5A, 5C). The knob 44 is manipulated by hand to rotate the catheter 6 so that the ultrasound probe points in the proper direction, as verified by looking through the eyepiece 16 (FIG. 2) of the endoscope 14.

As best illustrated in FIGS. 4 and 5, the connector assembly 40 includes a connector body 50 having a cylindrical recess 52 for receiving the wiper arm 42 of the potentiometer 36. The connector body 50 also includes a through bore 54 through which the catheter 6 may extend and a larger step bore 56 for receiving a stop member, as described in greater detail below. A latchpiece 60 having a cutout 62 (FIGS. 4B-D) is pivotally mounted on the connector body 50 by a screw 62 and nut 64 or some other conventional means.

As best illustrated in FIGS. 5A and 5B, a cylindrical stop member 70 is fixedly mounted on the catheter 6 by a set screw 72 or other conventional means. When the latchpiece 60 is open, as illustrated in FIG. 4C, the catheter 6 may be moved axially to place the stop member 70 within the cylindrical step bore 56. The latchpiece 60 is then closed to the position to the position illustrated in FIG. 4C, thereby capturing the stop member 70 within the bore 56. As a result, axial movement of the catheter 6 causes the connector assembly 40, and hence the wiper arm 42 of the potentiometer 36, to move correspondingly, thereby causing the resistance between leads 38 to vary as a function of the axial position of the ultrasound probe mounted on the catheter 6. It is significant that even when the catheter 6 is secured to the potentiometer 36 by the connector assembly 40, the catheter 6 may still be rotated by manipulating the knurled knob 44. As a result, the rotational position of the transducer body may vary with changes in the angle of the surface of the tissue being examined.

As mentioned above, it is important that the position transducer be secured to the catheter 6 in a manner that allows the catheter 6 to be disengaged from the position transducer. In operation, as described above, the endoscope 2 is normally inserted into the body of a patient and manipulated to place the window of the endoscope near the tissue of interest before the ultrasound probe and endoscope are fed through the biopsy channel of the endoscope. If the position transducer continuously engages the catheter 6, then the full-scale variations of the position transducer will cover virtually the entire length of the catheter 6 inserted in the endoscope 2. Axial movement of the ultrasound probe a relatively short distance, such as one inch, will thus produce a relatively small percentage of full-scale variation from the position transducer. As a result, the sensitivity of the position transducer will be, of necessity, somewhat limited. In contrast, by allowing the catheter 6 to be selectively engaged and disengaged from the position transducer, the sensitivity of the position transducer can be maximized. The full scale of the position transducer can cover a relatively small axial movement of the ultrasound probe, such as, for example, one inch. Thus, the output of the position transducer will vary full scale for relatively small axial movements of the catheter in order to maximize the sensitivity of the position transducer. Yet, even though the sensitivity of the position transducer is relatively high, the catheter may still move a relatively longer distance as the ultrasound probe and catheter are fed through the biopsy channel of the endoscope.

Although the embodiments illustrated in FIGS. 2-5 utilize a linear potentiometer, it will be understood that other devices, such as an optical encoder, may also be used.

The embodiments of FIGS. 2-5 utilize a position transducer that measures axial movement of the catheter on which the ultrasound probe is mounted. Thus, in these embodiments, the ultrasound image is generated by scanning the ultrasound probe axially along the tissue to be measured. As explained above with reference to FIG. 1, it will be understood that an ultrasound image may also be generated by rotating the catheter 6, thereby changing the rotational position of the ultrasound probe. However, rotational scanning requires that the rotational position of the ultrasound probe be measured in the same manner that the axial position of the ultrasound probe is measured in the embodiments of FIGS. 2-5. One embodiment of a rotational position sensor is illustrated in FIG. 6. Like the linear position sensors illustrated in FIGS. 2-5, the rotational position sensor illustrated in FIG. 6 may be disengaged from the catheter 6 when the ultrasound probe is being advanced through the biopsy channel of the endoscope. The rotational position transducer 80 also utilizes a potentiometer through which the catheter 6 extends. The rotational position transducer 80 includes a housing 82 which is carried by a connector mechanism. The connector mechanism 84 allows the position sensor to be mounted on a conventional endoscope 2 (FIG. 2) in the same manner as the embodiments of FIGS. 2-5. The connector 84 is screwed onto the proximal biopsy port 12 (FIG. 2) of the endoscope 14 by rotating a knurled knob 86. The knob 86 may rotate with respect to the housing 82, but after the connector 84 has been threaded into the biopsy port 12, it is locked against further rotation by actuating a locking lever 88. The locking mechanism actuated by the locking lever 88 is described in greater detail below.

As indicated above, the rotational position transducer 80 includes a potentiometer 90 mounted within the housing 82. The potentiometer has a hollow center bore through which the catheter 6 passes. An annular resistance element 94 of conventional design is coaxially positioned about the through bore 92 within the housing 82. A wiper contact 96 is carried by the potentiometer 90 and makes contact with the resistance element 94. The wiper contact 96 is electrically connected to a slip contact 98, which, in turn, makes electrical contact with a slip ring 100. The slip ring 100 is connected to an electrical contact 102. Other electrical contacts 104, 108 are connected to opposite ends of the resistance element 94. Thus, the resistance between contact 102 and the contacts 104, 108 varies with the rotational position of the potentiometer 90.

The potentiometer 90 has an axially extending portion 110 that terminates in a knurled knob 112. The knob 112 is rotated to rotate both the potentiometer 90 and catheter 6. The knob 112 has a through bore 114 that is partially threaded. The threaded through bore 114 receives a compression screw 116 rotated by knob 118. When the compression screw 116 is rotated with respect to knob 112, the knob 112 applies a radial force to the screw, thereby forcing it against the catheter 6 and locking the catheter 6 to the knob 112. Thus, when the screw 116 is rotated into threaded bore 114 of knob 112, the potentiometer 90 rotates with the catheter 6, while axial movement of the catheter 6 is prevented. When the screw 116 is rotated away from the knob 112, the catheter 6 is free to rotate and move axially with respect to the transducer 80.

Figure 6A:
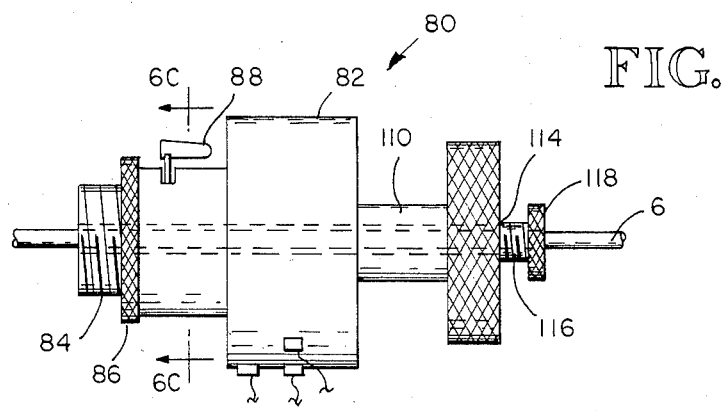
FIGS. 6A-6D are elevational, plan, and cross-sectional views of an ultrasound probe position transducer for providing a signal indicative of the rotational position of the ultrasound probe.
Figure 6B:
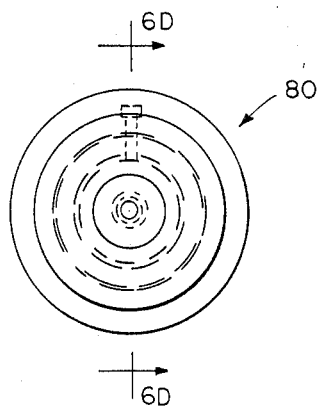
Figure 6C:
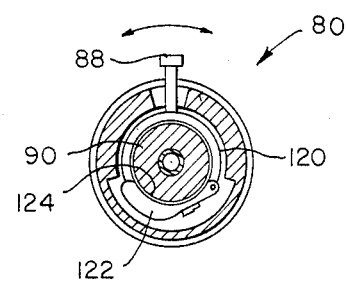
Figure 6D:
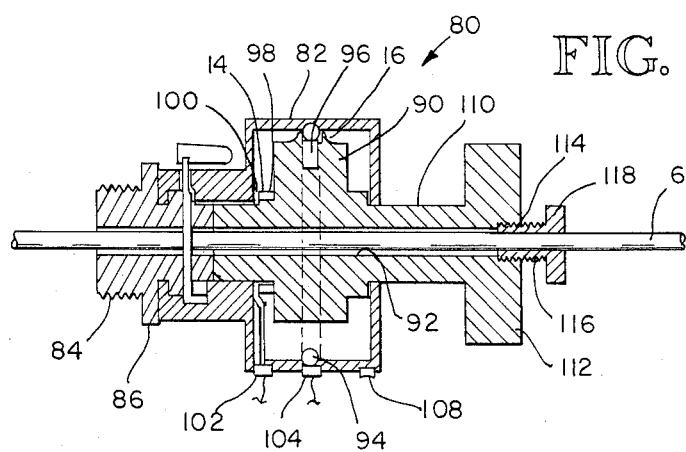

The locking mechanism actuated by the locking lever 88 is best illustrated in FIGS. 6A, 6C and 6D. The actuating lever 88 is connected to a circular member 120 having a tab 122 connected between its ends. A layer of frictional braking material 124 is positioned between the tab 122 and a reduced-diameter portion of the potentiometer body 90. In operation, rotation of the actuating lever 88 draws the ends of the circular member 120 away from each other, thereby causing the tab 122 to force the braking material 124 against the potentiometer body 90 and preventing rotation of the connector 84 with respect to the housing 82.

Figure 7:
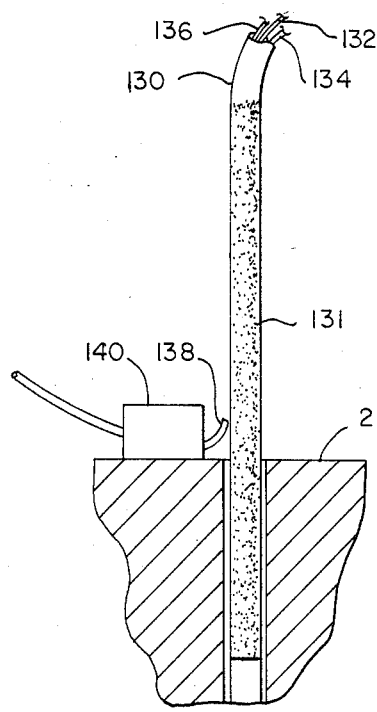
FIG. 7 is a cross-sectional view showing another embodiment of an ultrasound probe position transducer for providing a signal indicative of the axial position of the ultrasound probe.

Another embodiment of a position transducer for providing an electrical signal indicative of the axial position of a catheter is illustrated in FIG. 7. In this embodiment, a specially designed catheter 130 is coated with a resistive layer. The ends of the resistive layer are connected to respective conductor leads 132, 134 which extend from the end of the catheter 130 along with a multi-conductor lead 136 that is connected to the ultrasound transducer. A conductive wiper 138 extends from a mounting block 140 that is secured to the endoscope 2 adjacent the biopsy port. The resistive coating 131 on the catheter 130, along with the wiper 138, implements a potentiometer in which the resistance between the wiper 138 and each of the leads 132, 134 is indicative of the axial position of the catheter. Instead of coating the catheter 130 with a resistive material, the approach illustrated in FIG. 7 could also utilize a strip of resistive material attached to the outside of the catheter 130 along its length.

The position transducers illustrated in FIGS. 2–7 operate with manual scanning of the ultrasound transducer 8. However, mechanisms may also be employed to automatically scan the transducer and provide a signal indicative of its position. Automatic scanning allows both hands of the endoscopist to be occupied in holding the endoscope, turning its controls, or performing other necessary functions. Once the endoscopist manually positions the probe against the tissue of interest, the endoscopist can step on a foot switch to activate the automatic system to move the probe either axially or radially. When axial scanning is to be used, it is preferable that the probe be retracted rather than extended responsive to actuating the foot switch. The foot switch can then be once again activated to cause it to move outwardly in preparation for another scan. However, the probe should move outwardly at a slower rate than for retraction in order to ensure that the movement of the probe is under complete control and observation of the endoscopist in order to remove any possibility of puncturing the wall under observation.

Figure 8:
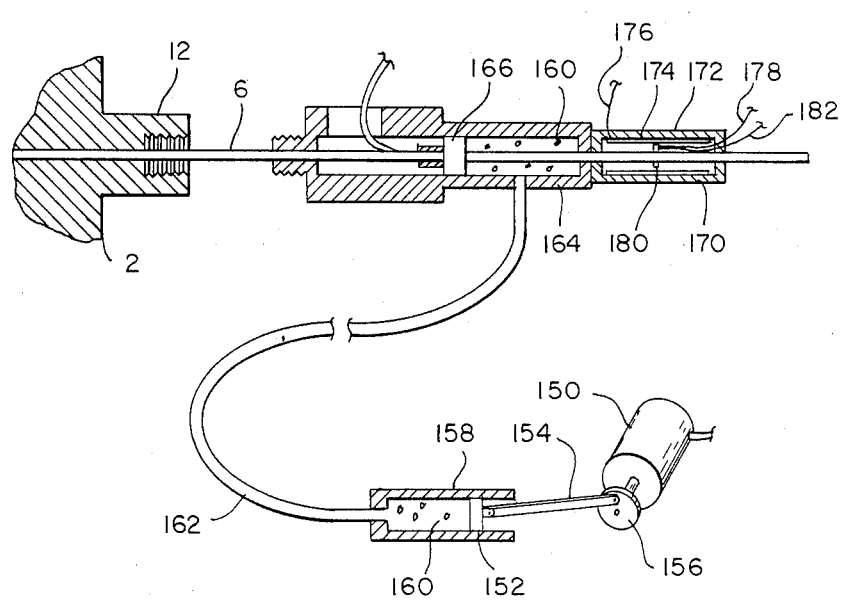
FIG. 8 is a schematic and cross-sectional view of a mechanism for automatically moving the ultrasound probe axially and providing a signal indicative of the axial position of the probe.

One embodiment for automatically scanning the biopsy probe axially is illustrated in FIG. 8. The embodiment of FIG. 8 utilizes hydraulic or pneumatic pressure to axially move the catheter 6 extending into the biopsy channel of an endoscope 2. A drive motor 150 drives a piston 152 to a piston rod 154 and crank 156. The piston 152 is mounted in a cylinder 158 containing hydraulic fluid or air 160. As the motor 150 rotates, the piston 152 moves into and out of the cylinder 158, thereby forcing fluid 160 into and out of a coupling tube 162.

The coupling tube 162 extends to a drive cylinder 164 mounted on the proximal biopsy port 12 of the endoscope 2. A drive piston 166 is mounted in the cylinder 164 and is secured to the catheter 6. As the fluid 160 is forced into and out of the coupling tube 162, the drive piston 166 moves back and forth in the cylinder 164, thereby causing the catheter 6 to move into and out of the biopsy channel.

The catheter 6 extends from the end of the cylinder 164 through an axial position transducer 170. The axial position transducer 170 may include a housing 172 having a layer of resistive material 174 coating its inner wall between a pair of conductor leads 176, 178. A conductive wiper 180 connected to lead 182 is mounted on the catheter 6. The resistance between lead 182 and the leads 176, 178 is thus indicative of the axial position of the catheter 6. If desired, the drive motor 150 can be a stepper motor in which the rotational position of the crank 156 can be precisely controlled in order to precisely control the axial position of the catheter 6. In operation, the endoscopist initiates the scan by stepping on a foot switch (not shown), thereby applying power to the drive motor 150. Drive motor 150 causes piston 152 to draw fluid (gas or liquid) 160 from the cylinder 164, thereby causing the drive piston 166 to move to the right, as illustrated in FIG. 8. The position of the transducer is measured by determining the resistance between lead 182 and lead 176 or lead 178.

The embodiment illustrated in FIG. 8 automatically scans the transducer probe externally by axially moving the catheter. However, the probe can also be scanned internally by applying fluid to the probe rather than to a piston at the biopsy port of the endoscope. As illustrated in FIG. 9, an ultrasound transducer 190 is mounted on a transducer support 192. The proximal end of the transducer support 192 frictionally engages the inside walls of a special catheter 194 at 196. A tube 198 extends through the end of the transducer support 192 and terminates in a cutout 200 in the transducer support 192. The catheter 194 acts as a cylinder and the transducer support 192 as a piston. Thus, when fluid flows in the catheter 194 outside the tube 198 to the right, as illustrated in FIG. 9A, the transducer support 192 is forced to the right. Under these circumstances, fluid to the right of the bearing area 196 is forced into the cutout 200 and through the tube 198. When fluid flows in the opposite direction, the fluid flowing through the tube 198 into the cutout 200 forces the transducer support 192 to the left, as illustrated in FIG. 9A. Conductor leads 202, 204 extend through the catheter 194 and through the transducer support 192 and are connected to the transducer 190.

As best illustrated in FIG. 9B, the catheter 194 has formed therein an elongated cutout covered by an acoustic window 208 positioned above the transducer 190. The transducer 190 thus moves back and forth beneath the acoustic window 208. The scanning mechanism illustrated in FIG. 9 produces a scanning action that is smoother and quicker than scanning the probe by axially moving the catheter. Axially moving the catheter requires significantly more force since the catheter drags against the wall of the biopsy channel, particularly when the endoscope is bent.

The scanning mechanism illustrated in FIG. 9 may be actuated by the mechanism illustrated in FIG. 10. The catheter 194 extends through a housing 210 containing a flexible bag 212 of fluid into which the tube 198 extends. The end of the catheter 194 forms a cylinder that receives a piston 214 that is driven by an actuating linkage 216 through a quick-disconnect coupling mechanism 218. The actuating arm 216 is, in turn, driven by a motor or pneumatic actuator and is coupled to a displacement transducer, such as the type illustrated in FIG. 8. As the piston 214 moves to the left, the fluid flowing through catheter 194 forces the transducer support 192 to the right, as illustrated in FIG. 9. Fluid displaced by the transducer support 192 is then forced into the tube 198 and expands the flexible bag 212. The position of the piston 214, and hence the position of the transducer support 192, are measured by the position transducer. When the piston 214 moves to the right, it draws fluid from the catheter 194, thereby causing the transducer support 192 to move to the left, as illustrated in FIG. 9. The vacuum created in the cutout 200 caused by moving the transducer support 192 to the left causes fluid to be drawn from the bag 212 into the tube 198. The embodiment of FIGS. 9 and 10 thus internally scans the transducer without scanning the probe to provide smooth and accurate scanning of the transducer.

Figure 11:
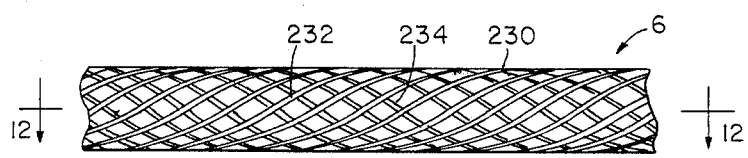
FIG. 11 is an elevational view showing the construction of the catheter to which the ultrasound probe is connected.
Figure 12:
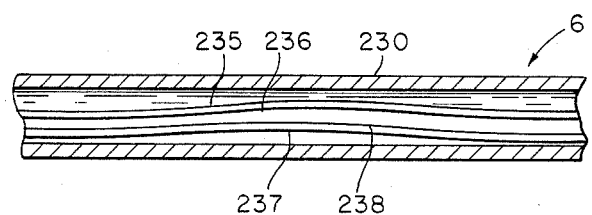
FIG. 12 is a cross-sectional view taken along the line 12—12 of FIG. 11.
Figure 13A:
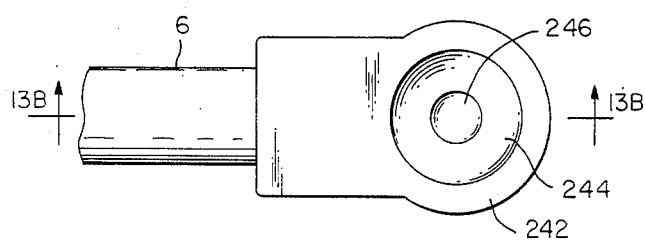
FIGS. 13A-D are plan and cross-sectional views of the ultrasound probe used in the endoscopically deliverable ultrasound imaging system.
Figure 13B:
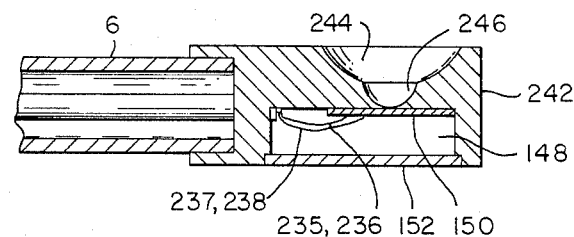
Figure 13C:
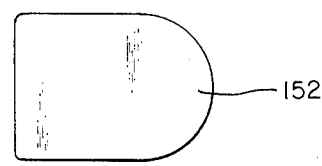
Figure 13D:
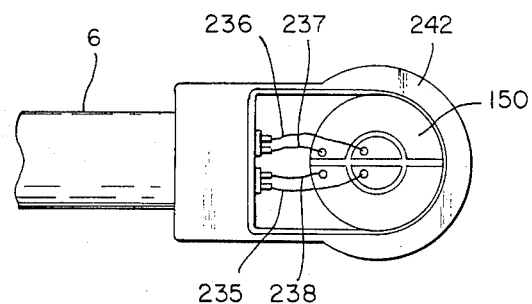

The catheter 6 used in the endoscopically deliverable ultrasound probe is illustrated in greater detail in FIGS. 11 and 12. The wall 230 of the catheter is formed by a conventional air-impermeable, flexible material which may be the same material used to form the outer casing of the endoscope 2. The catheter 6 should be relatively flexible so that it can follow the contour of the endoscope biopsy channel when the endoscope is positioned in many different positions. However, the catheter 6 must have sufficient axial and torsional rigidity so that the longitudinal or angular position of the ultrasound probe can be controlled by adjusting the longitudinal or angular position of the catheter 6 at the biopsy port 12. In order to provide the required torsional and axial rigidity, spirally wound reinforcement windings 232, 234 are embedded in the wall 230 of the catheter 6 and overlap each other 90 degrees. The spiral winding provides good torsional and axial rigidity, but allows the catheter 6 to remain flexible. Other configurations for the catheter 6 can, of course, also be used. For example, the spirally wound reinforcement windings 232, 234 can be tightly wound so that they alone form the cathether 6.

As best illustrated in FIG. 12, the interior of the catheter 6 is hollow, thereby allowing two pairs of leads 235, 236 and 237, 238 to pass through the catheter 6 to the ultrasound probe.

One embodiment of an ultrasound probe 240 is illustrated in FIGS. 13A–D. This embodiment of the ultrasound probe 240 is of a dual-element design that is capable of focusing in two distinct depth ranges. An ultrasound probe body 242 is mounted on the end of the catheter 240. The probe body 242 includes a pair of recesses 244, 246 having the shape of a partial sphere, with the radius of recess 244 being substantially greater than the radius of recess 246. The opposite face of the probe body 242 includes a semicylindrical recess 248 within which an ultrasound transducer 250 is mounted. The ultrasound transducer 250 is connected to the ultrasound imaging system by the leads 236–238 illustrated in FIG. 12. The recess 248 is enclosed by a cap 252 recessed into the ultrasound probe body 242.

The ultrasound probe body 242 may be formed of epoxy or other plastic material by injection molding. The catheter 6 is preferably introduced into the mold prior to the injection of the material forming the probe body so that the catheter 6 is integrally bonded to the probe body 242. The leads 236, 238 are then connected to appropriate points on the ultrasound transducer 250, as described in greater detail below. In order to minimize the energy loss of the transducer 250, the recess 248 is then preferably evacuated and sealed with the back cap 242.

As mentioned above, it is highly desirable for the connections to the ultrasound transducer 250 to be made to the rear face only. As illustrated in FIG. 14A, a conventional "back face connected only" transducer utilizes a thin, circular disk 252 of piezoelectric material fabricated in a conventional manner. Normally, the disk 252 will be cut from a much larger piece of piezoelectric material so that a large number of disks 260 are fabricated at the same time. The front face of the disk 252 contains a plating 254 over its entire surface, while the rear face of the disk 252 contains two semicircular plated areas 255, 256. Respective leads 257, 258 are connected to the semicircular plated areas 255, 256.

In the prior art embodiment illustrated in FIG. 14A, the entire piezoelectric disk 252 is polarized in the same direction throughout. In operation, the circular plated area 254 on the front face provides a surface for capacitively coupling the signal applied through leads 257, 258. As a consequence, one-half the drive signal is lost between one semicircular plated area 255 and the front plated area 254, and the other half of the drive signal is lost between the plated area 254 and the other semicircular plated area 256. Since the signal is flowing between one semicircular plated area and the plated area 254 in a direction opposite the direction of current flow between the plated area 254 and semicircular plated area 256, one-half of the piezoelectric disk 252 is in contraction, while the other half is in contraction. This mode is in contrast with the usual piezoelectric transducer operating mode where the entire transducer is in either contraction or expansion. Under this dual action, one-half the transducer radiates a wave that is 180 degrees out of phase with the other half of the transducer, thereby producing two main beam patterns instead of one. These two main beam patterns are undesirable for ultrasonic imaging.

As illustrated in FIG. 14B, a "back face only connected" transducer generating a single beam can be implemented by regional repolarization of the piezoelectric disk 252'. According to this technique, the disk 252' between the front face plating 254 and the semicircular rear face plated area 255 is polarized in a direction that is different from the polarization in the disk 252' between the front face plating 254 and the semicircular plated area 256. This repolarization allows both halves of the transducer to move in concert, even though opposite electrical polarities are applied to each half of the disk. The inventive "back face only connected" transducer illustrated in FIG. 14B can be manufactured as a single-element ultrasound transducer or as a dual-element ultrasound transducer that has two discrete ranges of focusing regions.

One embodiment of a dual-element ultrasound transducer 250' is illustrated in FIGS. 15A and 15B. It will be understood, however, that the ultrasound transducer 250 may be a single element or may have a number of elements in excess of two. The transducer 250' is formed by a thin, circular disc 260 of piezoelectric material fabricated in a conventional manner. Using photoresistive techniques, an etching pattern is deposited on each face of the disk 260. On the front face of the disc, the entire surface is coated with a plating 262 of metal. The etching pattern for the back face includes a pair of semiannular outer electrodes 264, 266 and a pair of semicircular inner electrodes 268, 270. The semiannular electrodes 264, 266 and the semicircular electrodes 268, 270 are separated form each other by a common diameter 272.

The transducer 250 is preferably fabricated by plating both the front face and the back face of the disk 260 with a metal, such as silver or gold. The plating is then etched away using conventional photoresistive techniques. A high-frequency signal applied between the leads 236, 238 causes the disc 260 to vibrate by the piezoelectric effect. In order to implement a relatively narrow ultrasound beam, most useful for focusing at relatively shallow depths, the signal is applied solely between leads 235 and 236. A relatively broad ultrasound beam, most useful for focusing at relatively large depths, is produced by applying the high-frequency signal between the leads 237 and 238.

As mentioned above, the piezoelectric disk 260 must be repolarized in order to allow the transducer 250' to generate a single ultrasound beam. The disk 260 may be repolarized by first connecting a DC power supply so that the positive terminal is connected to the back face electrodes 235–238 and the negative terminals connected to the front face plated area 262. The disk 260 is then emerged in oil heated to 100° C. and the voltage is adjusted to 600 volts (i.e., 2 kv/1 mm of thickness). After one hour in the heated oil with the voltage continuously applied, the disk is removed and allowed to cool for fifteen minutes. At the end of the fifteen-minute period, the leads are disconnected from the power supply. The leads are then connected to the power supply so that the back face electrodes 268, 264 are connected to the negative terminal of the DC power supply and the front face plated area 262 is connected to the positive terminal. The above steps are then repeated to repolarize the disk 260 between the front face plated area 262 and rear face electrodes 264, 268. It may be possible to apply a single polarizing voltage between the back face electrodes 235, 237 and 236, 238. However, since the polarizing voltage must be twice that of the polarizing applied between the front face and the back face, insulator breakdown or arcing can occur, allowing current to flow between the two pairs of back face plated areas.

Various techniques for focusing the ultrasound beam in the same manner that a lens focuses light are illustrated in FIGS. 16A and 16B. As illustrated in FIG. 16A, the characteristics of the material forming the probe body 242 in conjunction with the radius of curvature of the recesses 244, 246 controls the focusing of the ultrasonic beam emitted by the piezoelectric transducer 250. The curvatures are chosen so to produce focusing at various depths. When the inner portions 268, 270 (FIG. 15A) are excited, the ultrasound beam focuses in a region relatively close to the transducer 250 by virtue of the relatively small radius of curvature of the recess 246. When the outer plated portions 264, 266 (FIG. 15A) are excited, the ultrasound beam focuses a relatively longer distance from the ultrasound transducer 250 by virtue of the relatively longer radius of curvature of the recess 244.

The recesses 244, 246 are normally filled with a conventional impedance matching material, such as water or ultrasound gel. However, as illustrated in FIG. 16B, the recesses 244, 246 may be filled with other material 276, such as silicone rubber. The use of other materials, such as silicone rubber, provides further focusing since the material 276 has a speed of sound that is different from that of tissue. Consequently, the curvature 278 of the outer surface of the material 276 provides additional focusing action. Although the curvature 278 illustrated in FIG. 16B has a single radius of curvature, it will be understood that the curvature 278 of the material 276 could have two different radii to provide separate focusing for both the inner and other elements of the transducer. An additional advantage of the use of a material 276 have a convex surface is that the lens maintains acoustic contact with tissue better that does the lens shown in FIG. 16A.

The ultrasound probe 240 may also be a single element, as illustrated in FIGS. 17A and 17B. The single-element design utilizes a probe body 246' having a single-element ultrasound transducer 250" and a recess 244' having a single radius of curvature. The recess 244' is normally filled with an impedance matching material in the same manner as the embodiment of FIG. 16A. Like the embodiment of FIG. 16B, the recess 244' may be filled with another material 276', such as silicone rubber, as best illustrated in FIG. 17B.

Although the probe illustrated in FIGS. 13, 16, and 17 uses a "back face only connected" transducer, it will be understood that the probe may utilize a conventional transducer having its conductor leads connected between its front and back faces.

Figure 18:
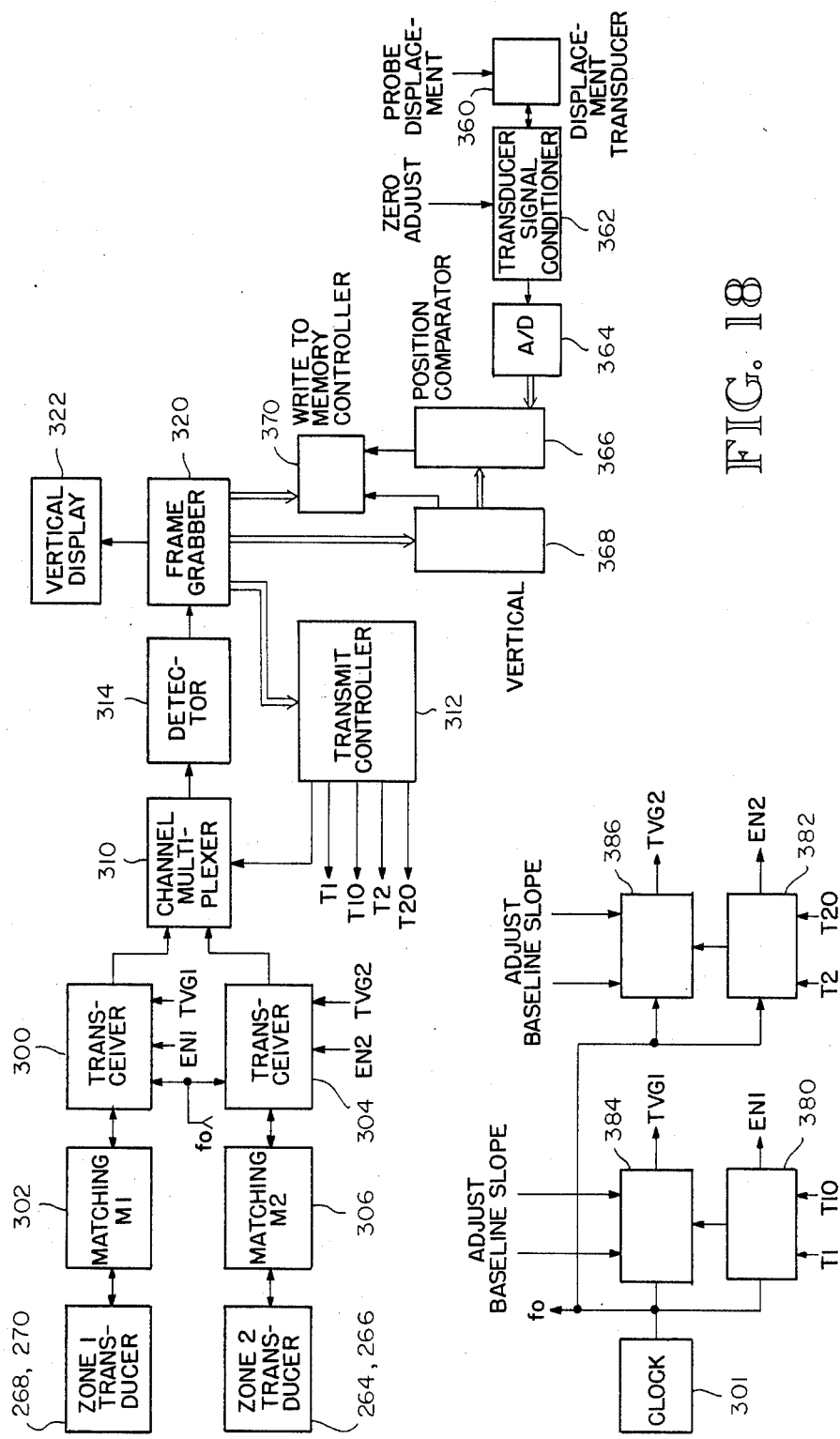
FIG. 18 is a schematic of one embodiment of a conventional ultrasound imaging system which may be connected to the ultrasound probes of FIGS. 1-17.
Figure 19:
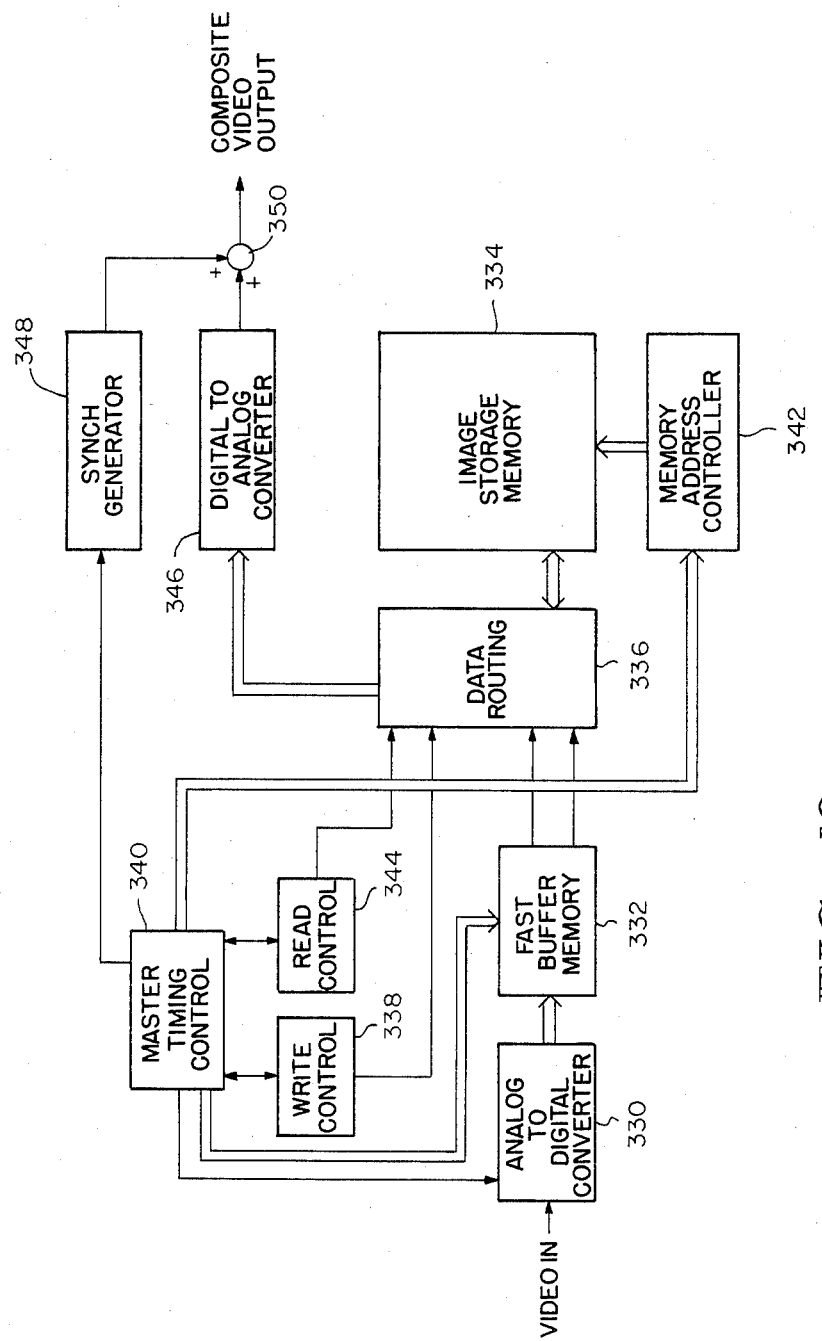
FIG. 19 is a schematic of an image capture and display memory circuit used in the ultrasound system of FIG. 18.

As mentioned above, the ultrasound probe may be connected to a conventional ultrasound imaging system that is normally used to display B-mode images. One embodiment of a suitable ultrasound imaging system is illustrated in FIGS. 18 and 19. With reference to FIG. 18, the inner zone elements 268, 270 (FIG. 15A) of the ultrasound transducer 250 are connected to a first transceiver 300 through a conventional matching network 302. Similarly, the outer zone elements 264, 266 of the transducer 250 are connected to a second transceiver 304 through a respective conventional matching network 306. The matching networks 302, 306 match the output and input impedances of the transceiver 304 to the impedance of the ultrasound transducer 250 in order to prevent reflected electromagnetic waves from being produced in the leads extending from the ultrasound system to the transducer 250. The matching networks 302, 306 also optimize the power transfer over a wide band of frequencies. The transceivers 300, 304 receive respective enable signals EN1, EN2 for triggering one of the transmitters in the enable transceiver, respective time varying gain control signals TVG1, TVG2 for controlling the gain of the receivers in the respective transceivers 300, 304 as a function of tissue depth to compensate for the greater attenuation from returns at greater tissue depths, and a local oscillator signal $f_0$ equal to the frequency of the transmitted ultrasound.

The outputs of the receivers in the respective transceivers 300, 304 are applied to a conventional multiplexer 310 that is controlled by a transmit controller 312 to apply the output of the zone 1 transceiver 300 to a detector 314 when returns are being received from relatively shallow tissue depths and to connect the output of the transceiver 304 to the detector 314 when returns from deeper tissues are being received. The detector 314 may be of conventional design, and it shifts the received ultrasound to base band by removing the carrier frequency $f_0$ from the received envelope. The output of the detector 314 is a video signal having an amplitude that is proportional to the intensity of the ultrasound returns. The initial portion of the video signal corresponds to depths close to the surface of the tissue being examined, while later portions of the video signal correspond to returns from deeper tissue levels.

The video signal at the output of the detector 314 is applied to an image frame storage system 320 so that when the video signal is written out to a video display monitor 322, the video signals for each position of the ultrasound probe represents a horizontal line of the image. The vertical position of each horizontal line on the display monitor 322 is controlled by the probe position transducers 10 (FIG. 2), 40 (FIGS. 3–5), and 80 (FIG. 6). As a result, each horizontal line on the display 322 provides information about the tissue depth, while the vertical position of the horizontal line in the display 322 indicates the position of the ultrasound probe. The intensity of each point on each horizontal line is proportional to the intensity of the ultrasound return from a depth corresponding to each such point. As a result, as the ultrasound probe is swept across the tissue, the vertical axis represents the distance along the surface of the tissue, whereas the horizontal axis represents the distance into the tissue. For the rotating ultrasound probe, as the probe rotates, the vertical axis represents the angle at which the ultrasound is directed into the tissue, while the horizontal axis represents the distance into the tissue. The image may also be displayed in a polar format in which the angle that a return is displayed on the CRT screen with respect to a fixed origin represents the transducer pointing angle, while the distance between the return and the origin represents the tissue depth.

The image frame storage system 320 is illustrated in greater detail in FIG. 19. The video signal at the output of the detector 314 is applied to a conventional analog-to-digital converter 330, which, as is well known in the art, periodically samples the video signal and outputs a byte of data indicative of each sample. The data from the analog-to-digital converter is applied to a fast buffer memory 332 of conventional design. The fast buffer memory 332 stores the digitized samples from the analog-to-digital converter 330 for subsequent processing.

Basically, the fast buffer memory 332 matches the sampling rate of the analog-to-digital converter 330 to the rate at which the data is called for by the remainder of the circuitry. After an entire line of data has been stored in the fast buffer memory 332, the line of data is written into an image storage memory 334 through a data routing network 336 to fill either an entire line or a partial line of memory 334. The data routing circuit 336 merely controls the flow of data into and out of the image storage memory 334, and it is controlled by a write control circuit 338. The write control circuit 338 is, in turn, controlled by a master timing control circuit 340 of conventional design. The address of the image storage memory into which data is written is controlled by a memory address controller 342, which is, in turn, controlled by the master timing control 340. Basically, the master timing control 340 causes the memory address controller 342 to output a relatively low address when an ultrasound pulse is initially transmitted. The master timing control 340 then causes the memory address controller 342 to periodically increment the image storage memory address in synchronism with the seat of data from the fast buffer memory 332. In this manner, the digitized video signal from the detector 314 is written into the proper memory address corresponding to a line of data.

The circuit for reading data from the image storage memory 334 and applying it to the digital display 322 operates in a continuous manner, and it time shares the control of the image storage memory with the image storage memory write cycle. Data is read from the image storage memory 334 by a read control circuit 344. The read control circuitry 344 continuously scans through the image storage memory 334 by producing a continuously increasing memory address from the memory address controller 342, thereby outputting the stored data pixel by pixel. Data from the image storage memory 334 is then applied through the data writing circuit 336 to a conventional digital-to-analog converter 346. The digital-to-analog converter 346 thus outputs the original video signal from the detector 314. In order to make this video signal usable by the video display 322, a synchronization signal is generated by a conventional sync generator 348 and added to the video signal by a conventional summing circuit 350. The composite video signal at the output of the summing circuit 350 is then applied to the video display 322.

Returning now to FIG. 18, the circuitry for controlling the vertical axis of the display 322 originates with one of the ultrasound probe position transducers, designated collectively as 360 in FIG. 18. The output of the position transducer 360 passes through a conventional signal conditioning circuit 362 to a conventional analog-to-digital converter 364. The signal conditioning circuit 362 provides level and impedance matching between the probe position transducer 360 and the analog-to-digital converter 364, and it allows the offset of the probe position signal to be adjusted. The analog-to-digital converter 364 periodically samples and then digitizes the probe position signal in a conventional manner. The analog-to-digital converter 364 thus outputs a byte of data indicative of the position of the ultrasound probe with respect to the endoscope. It will be understood that the position transducer 360 could be a digital encoder instead of a potentiometer. In such case, the signal conditioner 362 and analog-to-digital converter 364 would be unnecessary. Instead, the digital output from the encoder would be applied directly to the position comparator 366.

In one embodiment, the digital word indicative of the position of the ultrasound probe is applied to a conventional comparator 366 which also receives a digital word from a conventional vertical line detector 368. It will be recalled that the image storage memory 334 is being continuously swept horizontal line after horizontal line from the top of the video display 322 to the bottom. As each horizontal line scanned, a new vertical position occurs, and this information is read out of the memory address controller 342 and applied to the vertical detector 368. When the vertical position of the display scan from the vertical line detector 368 matches the position of the ultrasound probe, the position comparator 366 outputs a write enable signal to a memory control circuit 370. Memory control circuit 370 then causes the digitized video signal stored in the fast buffer memory 332 (FIG. 19) to be written into the line of image storage memory 334. However, the write enable circuit 370 causes data to be written into the image storage memory if a write enable signal WE is received from the transmit controller 312 at the same time that the write enable signal WE2 is received from the position comparator 366. The purpose of this is to allow the information to be stored in memory only when the horizontal position corresponds to the depth of the ultrasound return and the vertical position corresponds to the position of the ultrasound probe. Alternatively, the display axes can be reversed so that the vertical position corresponds to depth and the horizontal position corresponds to the position of the transducer. The image may also be displayed in polar coordinates instead of Cartesian coordinates. A polar display is particularly useful for rotational scanning, as in the embodiment of FIG. 6. The transmit controller 312 performs its function by generating output signals T1, T10, T2, T20 to enable circuits 380, 382. The enable circuits 380, 382 then generate respective enable signals EN1, EN2 in a conventional manner, which signals are then applied to respective transceivers 300, 304 to enable a signal to be transmitted, as described above. In this manner, the ultrasound signal is transmitted just prior to the start of each horizontal sweep. The enable circuits 380, 382 also generate outputs to conventional time varying gain control circuits 384, 386, respectively, to adjust the gain of the respective transceivers 300, 304 to compensate for signal attenuation with tissue depth. The base line and slope of the time gain control signals TVG1, TVG2 can be adjusted in a conventional manner.

We claim:

1. A system for ultrasonically imaging internal tissues through the biopsy channel of an endoscope, comprising:
   a catheter having a diameter that is sufficiently small to pass through said biopsy channel;
   an ultrasound probe mounted at one end of said catheter, said ultrasound probe having a maximum transverse dimension that is sufficiently small to pass through said biopsy channel, said ultrasound probe having a transversely directed beam pattern;
   position measuring means coupled to said catheter and adapted to be coupled to said endoscope for generating an ultrasound probe position signal indicative of the longitudinal position of said catheter with respect of said endoscope;
   latch means actuatable to manually disengage said catheter from said position measuring means so that said catheter can move longitudinally without varying said ultrasound probe position signal; and
   imaging means connected to said ultrasound probe by conductors extending through said catheter, said imaging means generating an ultrasound signal that is applied to said probe to generate an acoustic signal, said imaging means further receiving an ultrasound signal from said ultrasound probe corresponding to ultrasound acoustic signals reflected from said tissues to said ultrasound probe, said ultrasound imaging means generating said ultrasound image from said received ultrasound signal and from said ultrasound probe position signal.

2. The ultrasound imaging system of claim 1 wherein said position measuring means comprises:
   a linear potentiometer having a resistance between a pair of leads that varies according to the linear position of a potentiometer wiper contact arm, said potentiometer being adapted for mounting on said endoscope adjacent the proximal end of said biopsy channel; and
   a releasable fastener mounted on said wiper contact arm, said fastener releasably engaging said catheter so that the resistance between the leads of said potentiometer varies according to the longitudinal position of said catheter when said releasable fastener is engaged with said catheter.

3. The ultrasound imaging system of claim 2 wherein said releasable fastener comprises:
   a stop member secured to said catheter;
   a fastener body mounted on said wiper contact arm, said fastener body having a recess adapted to receive said stop member; and
   a latchpiece pivotally mounted on said fastener body, said latchpiece being movable to at least partially enclosed said recess to retain said stop member in said recess, thereby releasable securing said catheter to said potentiometer wiper contact arm.

4. The ultrasound imaging system of claim 3 wherein said latchpiece further includes an arcuate cutout to provide clearance for said catheter, thereby allowing said latchpiece to enclose substantially all of said stop member.

5. The ultrasound imaging system of claim 2 wherein the resistance between the leads of potentiometer is a linear function of the linear position of said wiper contact arm.

6. A system for ultrasonically imaging internal tissues through the biopsy channel of an endoscope, comprising:
   a catheter having a diameter that is sufficiently small to pass through said biopsy channel;
   an ultrasound probe mounted at one end of said catheter, said ultrasound probe having a maximum transverse dimension that is sufficiently small to pass through said biopsy channel, said ultrasound probe having a transversely directed beam pattern;
   an elongated layer of resistive material covering at least a portion of said catheter along its length;
   a conductor lead extending through said catheter from at least one end of said resistive material to an external location;
   a conductive wiper adapted for mounting on said endoscope and making contact with said resistive material so that the resistance between said conductor lead and said wiper is indicative of the longitudinal position of said catheter with respect to said endoscope; and imaging means connected to said ultrasound probe by conductors extending through said catheter, said imaging means generating an ultrasound signal that is applied to said probe to generate an acoustic signal, said imaging means further receiving an ultrasound signal from said ultrasound probe corresponding to ultrasound acoustic signals reflected from said tissues to said ultrasound probe, said ultrasound imaging means generating said ultrasound image from said received ultrasound signal and from said ultrasound probe position signal.

7. The ultrasound imaging system of claim 6 wherein said conductive wiper is adapted for mounting on said endoscope adjacent the proximal end of said endoscope and said resistive material covers said catheter in an area in which said catheter enters the biopsy channel of said endoscope when the distal end of said catheter is in a position to image internal tissues.

8. A system for ultrasonically imaging internal tissues through the biopsy channel of an endoscope, comprising:
   a catheter having a diameter that is sufficiently small to pass through said biopsy channel;
   an ultrasound probe mounted at one end of said catheter, said ultrasound probe having a maximum transverse dimension that is sufficiently small to pass through said biopsy channel, said ultrasound probe having a transversely directed beam pattern;
   a potentiometer housing adapted for mounting on said endoscope adjacent the proximal end of said biopsy channel;
   a rotary potentiometer mounted in said potentiometer housing, said potentiometer having an arcuate resistance element and a rotatable wiper contact slidable along said resistance element, said wiper contact being coupled to a hollow shaft through which said catheter extends, said hollow shaft being coaxial with said arcuate resistance element;
   a releasable fastener releasably securing said catheter to said hollow shaft so that said catheter and shaft rotate with each other; and
   imaging means connected to said ultrasound probe by conductors extending through said catheter, said imaging means generating an ultrasound signal that is applied to said prode to generate an acoustic signal, said imaging means further receiving an ultrasound signal from said ultrasound probe corresponding to ultrasound acoustic signals reflected from said tissues to said ultrasound probe, said ultrasound imaging means generating said ultrasound image from said received ultrasound signal and from said ultrasound probe position signal.

9. The ultrasound imaging system of claim 8 wherein said releasable fastener includes a compression screw having a hollow center axis threaded into the hollow shaft of said potentiometer in coaxial alignment with said shaft so that said catheter extends through the hollow center axis of said screw, said compression screw frictionally engaging said catheter when said compression screw is threaded into said shaft to secure said catheter to said shaft.

10. A system for ultrasonically imaging internal tissues through the biopsy channel of an endoscope, comprising:
   a catheter having a diameter that is sufficiently small to pass through said biopsy channel;
   an ultrasound probe having a tranversely directed beam pattern mounted at one end of said catheter, said ultrasound probe having a maximum transverse dimension that is sufficiently small to pass through said biopsy channel, said ultrasound probe having a probe casing mounted at the end of said catheter, said casing having at least one acoustically transparent area, a transducer support member mounted in said casing, an ultrasound transducer mounted on said transducer support member beneath said acoustically transparent area, and actuating means for selectively moving said transducer support member longitudinally within said casing, thereby longitudinally scanning said transducer;
   position measuring means coupled to said catheter and adapted to be coupled to said endoscope for generating an ultrasound probe position signal indicative of the longitudinal position of said catheter with respect to said endoscope;
   imaging means connected to said ultrasound probe by conductors extending through said catheter, said imaging means generating an ultrasound signal that is applied to said transducer to generate an acoustic signal, said imaging means further receiving an ultrasound signal from said ultrasound probe corresponding to ultrasound acoustic signals reflected from said tissues to said ultrasound probe, said ultrasound imaging means generating said ultrasound image from said received ultrasound signal and from said ultrasound probe position signal.

11. The ultrasound imaging system of claim 10 wherein said catheter includes a fluid channel extending along its length and communicating with the interior of said probe casing, and wherein said transducer support member includes a piston slidably engaging the inside wall of said probe casing, and wherein said actuating means includes fluid control means for selectively applying fluid to the interior of said catheter to cause said piston to move said transducer support member longitudinally in said probe casing.

12. The ultrasound imaging system of claim 11, further including a pressure release tube extending through the catheter and piston into the interior of said probe casing to allow said fluid to flow into and out of the distal end of said casing when fluid flowing through said catheter moves said piston.

13. The ultrasound imaging system of claim 11 wherein said actuating means comprise a drive piston slidably mounted in the interior of said catheter to force said fluid toward and away from said probe, said drive piston being coupled to an electromechanical actuator and to said position measuring means.

14. The ultrasound imaging system of claim 13, further including a flexible bag positioned outside said endoscope and a pressure release tube extending from said bag through said catheter and piston into the interior of said probe casing to allow said fluid to flow into and out of the distal end of said casing when fluid flowing said catheter moves said piston.

15. A system for ultrasonically imaging internal tissues through the biopsy channel of an endoscope, comprising:
   a catheter having a diameter that is sufficiently small to pass through said biopsy channel;
   an ultrasound probe having a tranversely directed beam pattern mounted at one end of said catheter, said ultrasound probe having a maximum transverse dimension that is sufficiently small to pass through said biopsy channel, said ultrasound probe having a probe body having a planar transducer mounting surface and a partially spherical recess positioned above said transducer mounting surface, an ultrasound transducer mounted on said transducer mounting surface, and an impedance matching material filling said partially spherical recess;

position measuring means coupled to said catheter and adapted to be coupled to said endoscope for generating an ultrasound probe position signal indicative of the longitudinal position of said catheter with respect to said endoscope; and imaging means connected to said ultrasound probe by conductors extending through said catheter, said imaging means generating an ultrasound signal that is applied to said transducer to generate an acoustic signal, said imaging means further receiving an ultrasound signal from said ultrasound probe corresponding to ultrasound acoustic signals reflected from said tissues to said ultrasound probe, said ultrasound imaging means generating said ultrasound image from said received ultrasound signal and from said ultrasound probe position signal.

16. The ultrasound imaging system of claim 15 wherein the probe body of said probe further includes a second partially spherical recess concentric with said first partially spherical recess, said second partially spherical recess having a radius of curvature that is smaller than the radius of curvature of said first partially spherical recess, and wherein the transducer of said probe includes outer and inner elements having respective diameters approximately equal to the diameters of said first and second partially spherical recesses, thereby allowing said probe to focus at at least two depth ranges.

17. The ultrasound imaging system of claim 16 wherein said transducer comprises a cylindrical plate of a piezoelectric material having first and second planar faces, said first planar face being plated with a metal over substantially its entire surface, said second planar face being plated with a metal in two semicircular areas having a diameter that is substantially smaller than the diameter of said cylindrical plate and in two separate arcuate areas surrounding said semicircular areas, said ultrasound imaging system being connected between the plating on said semicircular areas to focus at a relatively shallow depth and between the plating on said arcuate areas to focus at a relatively large depth, the piezoelectric material beneath the semicircular area and arcuate area on one side of said plate being polarized oppositely from the polarization of the piezoelectric material beneath the other semicircular and arcuate areas.

18. The ultrasound imaging system of claim 17 wherein said semicircular plated areas are separated from each other and said plated arcuate areas are separated from each other by a common diameter of said cylindrical plate.

19. The ultrasound imaging system of claim 15 wherein said ultrasound transducer comprises a cylindrical plate of piezoelectric material having first and second planar faces, said first planar face being plated with a metal over substantially its entire surface and said second planar face being plated with a metal in two separate semicircular areas between which said ultrasound imaging system is connected, the piezoelectric material beneath one of said semicircular areas being polarized oppositely from the polarization of the piezoelectric material beneath the other of said semicircular areas.

20. A catheter for allowing an ultrasound image to be made through the biopsy channel of an endoscope, comprising:

a tube having a diameter that is sufficiently small to pass through said biopsy channel, said tube having sufficient rigidity so that the position and orientation of the ends of the tube correspond to each other, said tube having sufficient flexibility to conform to the curved configuration of an endoscope biopsy channel;

an ultrasound probe mounted at one end of said tube, said ultrasound probe having a maximum transverse dimension that is sufficiently small to pass through said biopsy channel, said ultrasound probe having a transversely directed beam pattern;

position measuring means coupled to said tube and adapted to be coupled to siad endoscope for generating an ultrasound probe position signal indicative of the longitudinal position of said tube with respect to said endoscope; and latch means actuated to manually disengage said tube from said position measuring means so that said tube can move longitudinally without varying said ultrasound probe position signal.

21. The catheter of claim 20 wherein said position measuring means comprises:

a linear potentiometer having a resistance between a pair of leads that varies according to the linear position of a potentiometer wiper contact arm, said potentiometer being adapted for mounting on said endoscope adjacent the proximal end of said biopsy channel; and a releasable fastener mounted on said wiper contact arm, said fastener releasably engaging said tube as it exits from said biopsy port so that the resistance between the leads of said potentiometer varies according to the longitudinal position of said tube when said releasable fastener is engaged in said tube.

22. The catheter of claim 21 wherein said releasable fastener comprises:

a stop member secured to said tube;

a fastener body mounted on said wiper contact arm, said wiper body having a recess adapted to receive said stop member; and a latchpiece pivotally mounted on said fastener body, said latchpiece being movable to at least partially enclose said recess to retain said stop member in said recess, thereby releasably securing said tube to said potentiometer wiper contact arm.

23. The catheter of claim 22 wherein said latchpiece further includes an arcuate cutout to provide clearance for said tube, thereby allowing said latchpiece to enclose substantially all of said stop member.

24. The catheter of claim 21 wherein the resistance between the leads of said potentiometer is a linear function of the linear position of said wiper contact arm.

25. A catheter for allowing an ultrasound image to be made through the biopsy channel of an endoscope, comprising:

a tube having a diameter that is sufficiently small to pass through said biopsy channel, said tube having sufficient rigidity so that the position and orientation of the ends of the tube correspond to each other, said tube having sufficient flexibility to conform to the curved configuration of an endoscope biopsy channel;

an ultrasound probe mounted at one end of said tube, said ultrasound probe having a maximum transverse dimension that is sufficiently small to pass through said biopsy channel, said ultrasound probe having a transversely directed beam pattern;

an elongated layer of resistive material covering at least a portion of said tube along its length;

a conductor lead extending through said tube from at least one end of said resistive material to an external location; and a conductive wiper adapted for mounting on said endoscope at a location that allows said wiper to make contact with said resistive material when the distal end of said tube is in a position to image internal tissues so that the resistance between said conductor lead and said wiper is indicative of the longitudinal position of said tube with respect to said endoscope.

26. The catheter of claim 25 wherein said conductive wiper is adapted for mounting on said endoscope adjacent the proximal end of the biopsy channel of said endoscope, and said resistive material covers said tube in an area in which said tube enters the biopsy channel of said endoscope when the distal end of sid tube is in a position to image internal tissues.

27. A catheter for allowing an ultrasound image to be made through the biopsy channel of an endoscope, comprising:

a tube having a diameter that is sufficiently small to pass through said biopsy channel, said tube having sufficient rigidity so that the position and orientation of the ends of the tube correspond to each other, said tube having sufficient flexibility to conform to the curved configuration of an endoscope biopsy channel;

an ultrasound probe mounted at one end of said tube, said ultrasound probe having a maximum transverse dimension that is sufficiently small to pass through said biopsy channel, said ultrasound probe having a transversely directed beam pattern;

a potentiometer housing adapted for mounting on said endoscope adjacent the proximal end of said biopsy channel;

a rotary potentiometer mounted in said potentiometer housing, said potentiometer having an arcuate resistance element and a rotatable wiper contact slidable along said resistance element, said wiper contact being coupled to a hollow shaft through which said tube extends, said hollow shaft being coaxial with said arcuate resistance element; and a releasable fastener releasably securing said tube to said hollow shaft so that said tube and shaft rotate with each other.

28. The catheter of claim 27 wherein said releasable fastener includes a compression screw having a hollow center axis threaded into the hollow shaft of said potentiometer in coaxial alignment with said shaft so that tube extends through the hollow center axis of said screw, said compression screw frictionally engaging said tube when said compression screw is threaded into said shaft to secure said tube to said shaft.

29. A catheter for allowing an ultrasound image to be made through the biopsy channel of an endoscope, comprising:

a tube having a diameter that is sufficiently small to pass through said biopsy channel, said tube having sufficient rigidity so that the position and orientation of the ends of the tube correspond to each other, said tube having sufficient flexibility to conform to the curved configuration of an endoscope biopsy channel;

an ultrasound probe having a transversely directed beam pattern mounted at one end of said tube, said ultrasound probe having a maximum transverse dimension that is sufficiently small to pass through said biopsy channel, said ultrasound probe having a probe casing mounted at the end of said tube, said casing having at least one acoustically transparent area, a transducer support member mounted in said tube, an ultrasound transducer mounted on said transducer support member beneath said acoustically transparent area, and actuating means for selectively moving said transducer support member longitudinally within said tube, thereby longitudinally scanning said transducer; and position measuring means coupled to said tube and adapted to be coupled to said endoscope for generating an ultrasound probe position signal indicative of the position of said tube with respect to said endoscope.

30. The catheter of claim 29, further including a fluid channel extending along the length of said catheter and communicating with the interior of said probe casing, and wherein said transducer support member includes a piston slidably engaging the inside wall of said probe casing, and wherein said actuating means includes fluid control means for selectively applying fluid to the interior of said catheter to cause said piston to move said transducer support member longitudinally in said probe casing.

31. The catheter of claim 30, further including a pressure release tube extending through said catheter and piston into the interior of said probe casing to allow said fluid to flow into and out of the distal end of said casing when fluid flowing through said catheter moves said piston.

32. The catheter of claim 30 wherein said actuating means comprise a drive piston slidably mounted in the interior of said catheter to force said fluid toward and away from said probe, said drive piston being coupled to an electromechanical actuator and to said position measuring means.

33. A catheter for allowing an ultrasound image to be made through the biopsy channel of an endoscope, comprising:

a tube having a diameter that is sufficiently small to pass through said biopsy channel, said tube having sufficient rigidity so that the position and orientation of the ends of the tube correspond to each other, said tube having sufficient flexibility to conform to the curved configuration of an endoscope biopsy channel;

an ultrasound probe having a transversely directed beam pattern mounted at one end of said tube, said ultrasound probe having a maximum transverse dimension that is sufficiently small to pass through said biopsy channel, said ultrasound probe having a probe body having a planar transducer mounting surface and a partially spherical recess positioned above said transducer mounting surface, an ultrasound transducer mounted on said transducer mounting surface, and an impedance matching material filling said partially spherical recess; and position measuring means coupled to said tube and adapted to be coupled to said endoscope for generating an ultrasound probe position signal indicative of the position of said tube with respect to said endoscope.

34. The catheter of claim 33 wherein the probe body of said probe further includes a second partially spherical recess, said second partially spherical recess having a radius of curvature that is smaller than the radius of curvature of said first partially spherical recess, and wherein the transducer of said probe includes outer and inner elements having respective diameters approximately equal to the diameters of said first and second partially spherical recesses, thereby allowing said probe to focus at at least two depth ranges.

35. The catheter of claim 34 wherein said transducer comprises a cylindrical plate of a piezoelectric material having first and second planar faces, said first planar face being plated with a metal over substantially its entire surface, said second planar face being plated with a metal in two separate semicircular areas having a diameter that is substantially smaller than the diameter of said cylindrical plate and in two separate arcuate areas surrounding said semicircular areas, each of said plated areas being connected to leads extending from said probe through said tube so that an ultrasound signal applied between the plating on said semicircular areas causes said probe to focus at a relatively shallow depth and an ultrasound signal applied between the plating on said arcuate areas causes said probe to focus at a relatively large depth, the piezoelectric material beneath the semicircular area and arcuate area on one side of said plate being polarized oppositely from the polarization of the piezoelectric material beneath the other semicircular and arcuate areas.

36. The catheter of claim 35 wherein said semicircular plated areas are separated from each other and said plated arcuate areas are separated from each other by a common diameter of said cylindrical plate.

37. The catheter of claim 33 wherein said ultrasound transducer comprises a cylindrical plate of piezoelectric material having first and second planar faces, said first planar face being plated with a metal over substantially its entire surface, and said second planar face being plated with a metal in two separate semicircular areas, the piezoelectric material beneath one of said semicircular areas being polarized oppositely from the polarization of the piezoelectric material beneath the other of said semicircular areas, said catheter further including a pair of leads extending between respective semicircular plated areas of said probe through said tube.

38. An ultrasound probe for generating an ultrasound acoustic signal and receiving reflected ultrasound acoustic signals, comprising:
a probe body having a planar transducer mounting surface and first and second partially spherical recesses positioned above said transducer mounting surface, said second partially spherical recess having a radius of curvature that is smaller than the radius of curvature of said first partially spherical recess;
an ultrasound transducer mounted on said transducer mounting surface, said transducer having outer and inner elements having respective diameters approximately equal to the diameter of said first and second partially spherical recesses ; and
an impedance matching material filling said partially spherical recess.

39. The ultrasound probe of claim 38 wherein said transducer comprises a cylindrical plate of a piezoelectric material having first and second planar faces, said first planar face being plated with a metal over substantially its entire surface, said second planar face being plated with a metal in two separated semicircular areas having a diameter that is substantially smaller than the diameter of said cylindrical plate and in two arcuate areas surrounding said semicircular areas, said semicircular areas causing said probe to focus at a relatively shallow depth when an ultrasound signal is applied between said semicircular areas, and said arcuate plated areas causing said probe to focus at a relatively large depth when an ultrasound signal is applied between said arcuate plated areas, the piezoelectric material beneath the semicircular area and arcuate area on one side of said plate being polarized oppositely from the polarization of the piezoelectric material beneath the other semicircular and arcuate areas.

40. The ultrasound probe of claim 39 wherein said semicircular plated areas are separated from each other and said plated arcuate areas are separated from each other by a common diameter of said cylindrical plate.

41. An ultrasound probe for generating an ultrasound acoustic signal and receiving reflected ultrasound acoustic signals, comprising:
a probe body having a planar transducer mounting surface and a partially spherical recess positioned above said transducer mounting surface;
an ultrasound transducer mounted on said transducer mounting surface, said ultrasound transducer including a cylindrical plate of piezoelectric material having first and second planar faces, said first planar face being plated with a metal over substantially its entire surface, and said second planar face being plated with a metal with two separate semicircular areas, the piezoelectric material beneath one of said semicircular areas being polarized oppositely from the polarization of the piezoelectric material beneath the other of said semicircular areas; and an impedance matching material filling said semicircular areas partially spherical recess.

42. An ultrasound transducer for generating an ultrasound acoustic signal from an ultrasound electric signal and for generating an ultrasound electric signal from a received ultrasound acoustic signal, said transducer comprising a cylindrical plate of piezoelectric material having first and second planar faces, said first planar face being plated with a metal over substantially its entire surface, and said second planar face being plated with a metal in two separate semicircular areas between which said ultrasound electric signal is applied or generated, the piezoelectric material between said first planar face and one semicircular area of said second planar face being polarized opposite to the polarization of the piezoelectric material between said first planar face and the other semicircular area of said second planar face.

43. The ultrasound transducer of claim 42 wherein said semicircular areas have a diameter that is substantially smaller than the diameter of said cylindrical plate, said transducer further including two separate arcuate areas surrounding said semicircular areas, thereby allowing said transducer to focus at a relatively shallow depth when said electrical signal is applied to or generated between said semicircular plated areas and allowing said transducer to focus at a relatively large depth when said ultrasound electric signal is applied to or generated between said arcuate areas.

44. The transducer of claim 43 wherein said semicircular plated areas are separated from each other and said plated arcuate areas are separated from each other by a common diameter of said cylindrical plate.

* * * * *